US00PP31177P3

(12) United States Plant Patent
Wagner, Sr.

(10) Patent No.: US PP31,177 P3
(45) Date of Patent: Dec. 3, 2019

(54) ***EREMOCHLOA OPHIUROIDES* (MUNRO) HACK PLANT NAMED 'SS-0705'**

(50) Latin Name: ***Eremochloa ophiuroides* (Munro) Hack**
Varietal Denomination: SS-0705

(71) Applicant: Tobey Andrew Wagner, Sr., Mount Pleasant, SC (US)

(72) Inventor: Tobey Andrew Wagner, Sr., Mount Pleasant, SC (US)

( * ) Notice: Subject to any disclaimer, the term of this patent is extended or adjusted under 35 U.S.C. 154(b) by 335 days.

(21) Appl. No.: 14/757,135

(22) Filed: Nov. 24, 2015

(65) Prior Publication Data

US 2016/0150712 P1 May 26, 2016

Related U.S. Application Data

(60) Provisional application No. 62/123,684, filed on Nov. 24, 2014.

(51) Int. Cl.
*A01H 5/12* (2018.01)

(52) U.S. Cl.
USPC ..... Plt./388

(58) Field of Classification Search
USPC ..... Plt./388
CPC ..... A01H 5/12
See application file for complete search history.

*Primary Examiner* — Annette H Para
(74) *Attorney, Agent, or Firm* — Myers Bigel, P.A.

(57) ABSTRACT

A new and distinct variety of Centipedegrass named 'SS-0705', is characterized by its green stolons, white flowers, short inflorescence, short and narrow leaf blades, compared to other Centipedegrass varieties.

6 Drawing Sheets

Latin name of the genus and species: The Latin name of the genus and species of the novel variety disclosed herein is *Eremochloa ophiuroides* (Munro) Hack and therefore characterizes a new and distinct perennial variety of Centipedegrass.

Variety denomination: The inventive variety of *Eremochloa ophiuroides* (Munro) Hack disclosed herein has been given the variety denomination 'SS-0705'.

BACKGROUND OF THE INVENTION

The present invention relates to a new and distinct perennial variety of *Eremochloa ophiuroides* (Munro) Hack.

'SS-0705' is the selection of *Eremochloa ophiuroides* found in 2007 in a cemetery in Covington, Ga., which is located in the North Georgia area. The cemetery contained mowed or cultivated grasses including cultivated centipedegrass and "SS-0705 was identified as a mutant in that it was distinctly different from the centipedegrass that was growing nearby. The exact pedigree of 'SS-0705' is unclear as centipedegrass is cultivated throughout the cemetery where 'SS-0705' was found. Specifically, 'SS-0705' was selected due to its distinct green color runners (also called stolons), leaves with no purple color and very good fall color retention. 'SS-0705' has been evaluated in FL, TX, NC, GA and MS in test plot areas in 2008 and 2009. Primary characteristics of the 'SS-0705' are short leaf blade length, short inflorescence and totally green stolons and leaves. 'SS-0705' has demonstrated excellent fall color retention, good cold hardiness, exhibiting green stolons. The rate of growth is medium, exhibiting low aggressiveness, which is beneficial to a low maintenance grass. 'SS-0705' is so identified in pictures and morphological and agronomic charts of this disclosure. It is anticipated that the plant of this invention will be marketed under the synonym 'Covington' as a trade name.

SUMMARY OF THE INVENTION

Asexual propagation of the new cultivar was first accomplish by stolon cuttings in Covington, Ga.

'SS-0705' is a distinctive variety of *Eremochloa ophiuroides* (Munro) Hack, having a light green color (10 GY 6/4 on a Munsell Color Chart), short leaf length, short inflorescences, average lateral growth rates and good cold tolerance. 'SS-0705' is propagated primarily by sprigs, rhizomes, plantlets or turf sod, but it can be propagated by seed also. 'SS-0705' is estimated to be adapted for US in zones 7-11 of the USDA Plant Hardiness Zone Map.

DESCRIPTION OF THE NEW VARIETY

Figure 1:
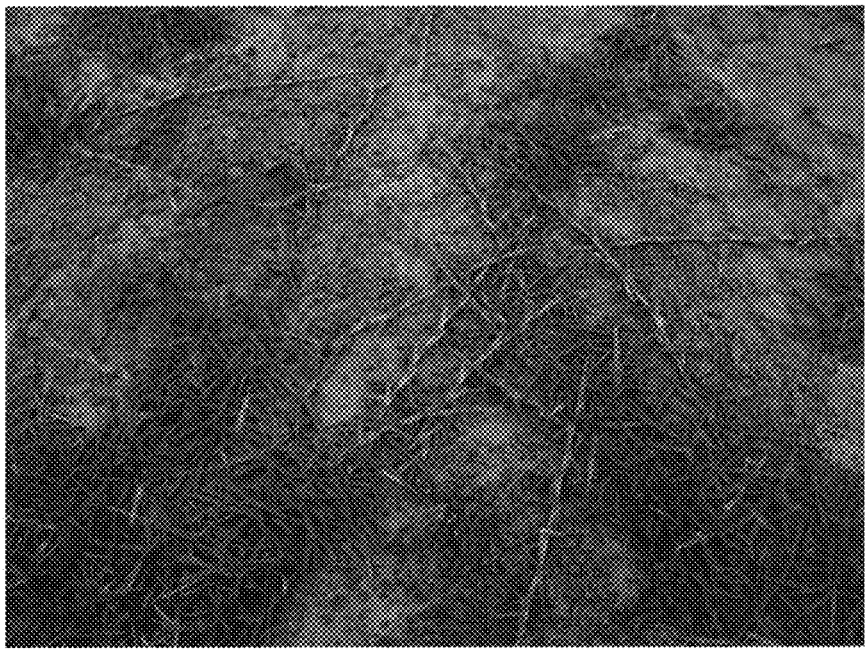
FIG. 1: 'SS-0705' green stolons detail.
Figure 2:
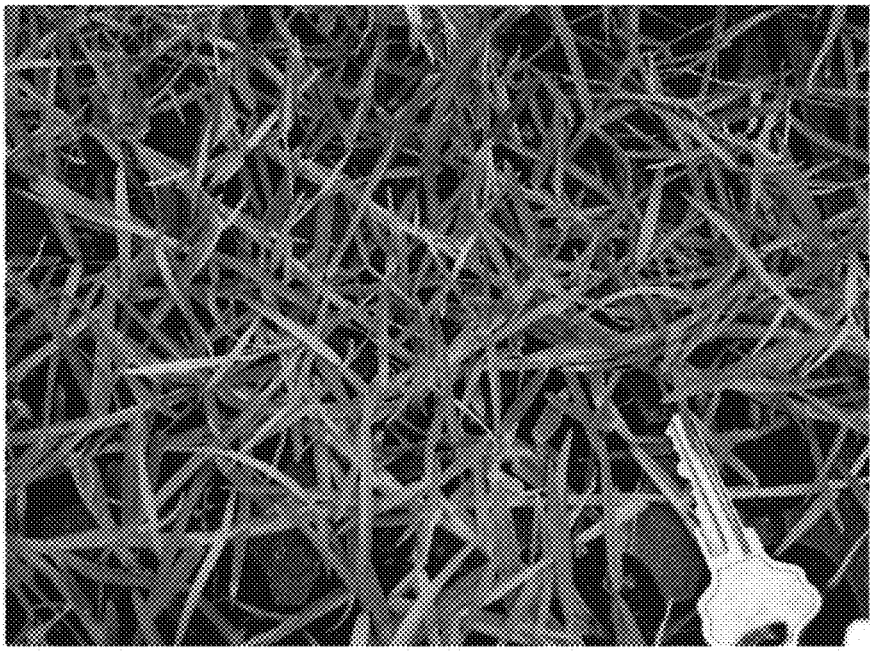
FIG. 2: 'SS-0705' leaves with no reddish/light purple color to it.
Figure 3:
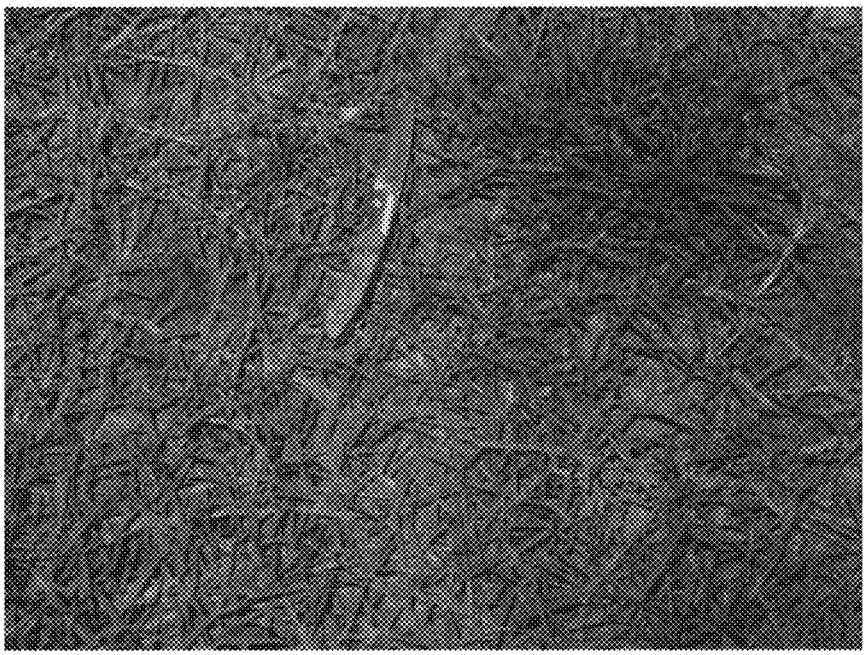
FIG. 3: Green stolons and leaves of 'SS-0705'.

The following is a detailed description of the new grass variety, based upon observations of the plant grown in field plots at a research area located near Starkville, Miss. 'SS-0705' is an exceptional Centipede grass cultivar with a light green color (10 GY 6/4 on a Munsell Color Chart). 'SS-0705' is an attractive Centipede grass exhibiting good lateral growth rate and high internode density. Leaf blades are completely green, with no tint of reddish/light purple color (FIGS. 2 and 3). 'SS-0705' has only green stems and runners (FIG. 1) making it a unique grass. 'SS-0705' performs better in warmer climates and although it has good cold tolerance is best suited for Plant Heat Zones 8-11. 'SS-0705' is a lower maintenance grass due to its low aggressiveness and its relative lower Nitrogen fertilization requirements, compared to other warm season grasses like *Zoysias* and Bermudas. 'SS-0705' is adapted to soils with low pH (<6.0) and to moderate shade. 'SS-0705' has an excellent blocking ability when harvested at a sod farm, due to its strong root and stolons which combined produce a perfect net forming a stable piece of sod.

Dimensions of Morphological Structures

'SS-0705' was compared to an experimental Centipedegrass and to 'Common Centipede' and 'TifBlair' in a study planted near Starkville, Miss. in 2008. Each variety was planted in 1 gallon pots, using potting mix: Redi-earth Plug and Seedling Mix (Sungro Horticulture, Bellevue, Wash.) and were kept at a green-house to produce plant material for morphological evaluations. Plant material was collected using a completely random experiment design with 4 replications (pots). Greenhouse complex had natural sunlight conditions. The pots were allowed to grow for 4 weeks, and then were clipped once to encourage density and stolon development. They were allowed to grow un-mowed for another 4 weeks before measurement. The leaf blade measurements were conducted from April 1$^{st}$ to Apr. 30, 2008. One hundred and forty randomly selected leaf blades from each cultivar were measured for length and width. Width was measured at the widest point of the blade. The internode measurements were conducted in the same period. All the stolons that grew off each pot were used to measure the internode diameter and internode length. The inflorescence measurements were conducted from September 2009 to November 2009. Thirty seed-heads were randomly selected from each cultivar. The Analysis of Variance (ANOVA) indicated that cultivars differed significantly for most variables measured (Table 1).

TABLE 1

Analysis of Variance for Centipedegrass cultivars comparisons conducted during the 2008 and 2009 growing seasons.

| | Mean Squares of the traits | | | |
|---|---|---|---|---|
| Source | ID (mm) | IL (mm) | LW (mm) | LL (mm) |
| Variety | 7.0** | 664.5** | 31.1* | 42334.4** |
| Error | 0.1 | 33.7 | 4.6 | 558.1 |
| CV | 12.0 | 39.5 | 42.0 | 33.7 |
| | Mean Squares of the traits | | | |
| Source | TIL (mm) | RL (mm) | PL (mm) | NSR |
| Variety | 249.5** | 162.3** | 71.7** | 260.1** |
| Error | 13.9 | 2.9 | 10.7 | 4.7 |
| CV | 13.8 | 14.1 | 21.8 | 15.1 |

ID — Internode Diameter, IL — Internode Length, LL — Leaf Width (mm), LW — Leaf Length (mm), TIL — Total Inflorescence Length (mm), RL — Raceme Length (mm), PL — Peduncle Length (mm), NSR ? Number of Spikelets per Raceme.
*Significant at 5% level **Significant at 1% level

TABLE 2

Morphological measurements from unmown greenhouse pots - April, 2008.

| Cultivar | Internode diameter (mm) | Internode length (mm) | Leaf blade width (mm) | Leaf blade length (mm) |
|---|---|---|---|---|
| 'SS-0607' | 2.3 | 16.3 | 5.5 | 82.4 |
| 'SS-0705' | 1.9 | 13.1 | 4.8 | 57.7 |
| LSD (0.05) | 0.1 | 1.4 | 0.5 | 5.6 |
| Number of observations | 140 | 140 | 140 | 140 |

TABLE 3

Inflorescence measurements from unmown greenhouse pots - November, 2009.

| Cultivar | Total inflorescence length[a] - cm | Raceme length[b] - cm | Peduncle length[c] - cm | Number of spikelets per raceme[d] |
|---|---|---|---|---|
| 'Common Centipede' | 9.41 | 4.18 | 5.23 | 15.5 |
| 'SS-0607' | 9.14 | 4.10 | 5.05 | 15.8 |
| 'TifBlair' | 8.26 | 3.70 | 4.56 | 13.9 |
| 'SS0705' | 7.40 | 3.25 | 4.15 | 12.1 |
| LSD (0.05) | 0.60 | 0.27 | 0.53 | 0.11 |

[a]Total inflorescence length is the mean of 30 observations per cultivar including the raceme peduncle measured from the first node.
[b]Raceme length is the mean of 30 observations per cultivar.
[c]Peduncle length is the mean of 30 observations per cultivar measured from the base of the raceme to the first node.
[d]Number of spikelets per raceme is the mean of 30 observations per cultivar determined by count.

Cultivars showed significant differences on the majority of the analyzed morphological characteristics (Table 1). Internode Diameter (ID), Internode Length (IL), Leaf Length (LL), Total Inflorescence Length (TIL), Raceme Length (RL), Peduncle Length (PL) and Number of Spikelets per Raceme (NSR) were significantly different at 1% level (Table 1). The evaluations were well conducted and produced reliable results as demonstrated by the low Coefficients of Variation (CV) (Table 1).

'SS-0705' had a smaller internode diameter (1.90 mm) and a shorter internode length (13.1 mm) when compared to 'SS-0607' (2.3 mm and 16.3 mm, respectively) (Table 2). 'SS-0705' also had a shorter leaf blade length (57.70 mm) compared to 'SS-0607' (82.4 mm) (Table 2). In addition, 'SS-0705' had a narrower leaf blade width (4.8 mm) compared to 'SS-0607' (5.5 mm) (Table 2). The internode diameter, length and leaf blade length and width differences between the two varieties were significantly different at 5% level (Table 2). A second distinguish characteristic of 'SS-0705' is that it exhibits only green stolons, (FIG. 1) and its leaves are green with no reddish or purple tint to it (FIGS. 2 and 3).

Figure 4:
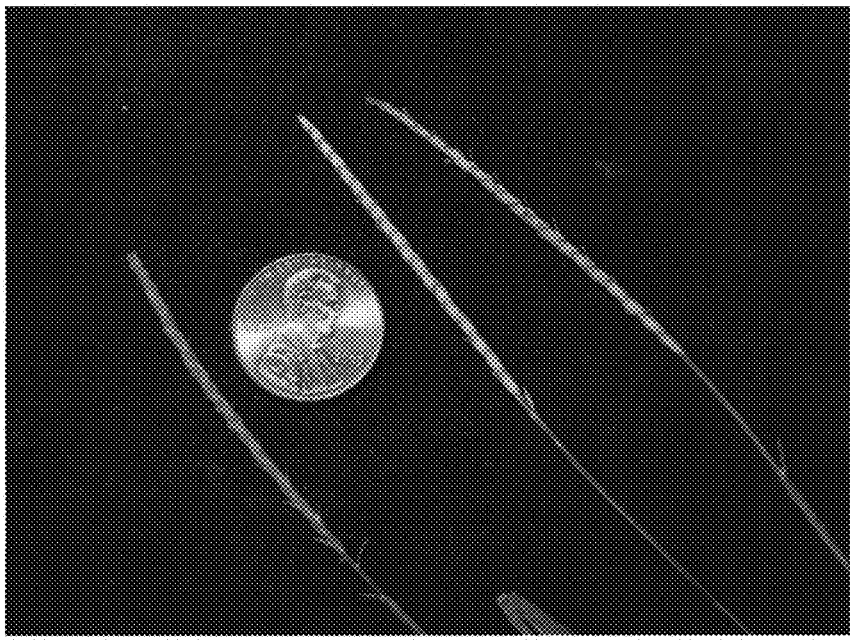
FIG. 4: 'SS-0705' white seed-heads.

'SS-0705' has short inflorescences; its total inflorescence length (7.40 cm) was the shortest among all tested lines and varieties (Table 3). The total inflorescence length of 'SS-0705' was significantly shorter than the total inflorescence length of 'TifBlair' (8.26 cm), 'SS-0607' (9.14 cm) and 'Common Centipede' (9.41 cm) (Table 3). 'SS-0705' total inflorescence length was significantly different to all other tested entries because the differences were bigger than the LSD (0.05), which was 0.60 cm. The inflorescence of 'SS-0705' is white (FIG. 4) and can be easily seen by a person walking the field.

A more detailed examination of the inflorescence structures, shows 'SS-0705' has the shortest raceme length (3.25 cm) and peduncle length (4.15 cm) among all tested varieties (Table 3). 'TifBlair's raceme length (3.70 cm) and peduncle length (4.56 cm); 'Common Centipede's raceme length (4.18 cm) and peduncle length (5.23 cm) and 'SS-0607's raceme length (4.10 cm) and peduncle length (5.05 cm) were statistically longer than 'SS-0705' (Table 3). In addition to having the shortest raceme and peduncle length among the compared varieties, 'SS-0607' also exhibits the smallest number of spikelets per raceme (12.1), which was statistically different than all other entries in that test (Table 3).

Figure 5:
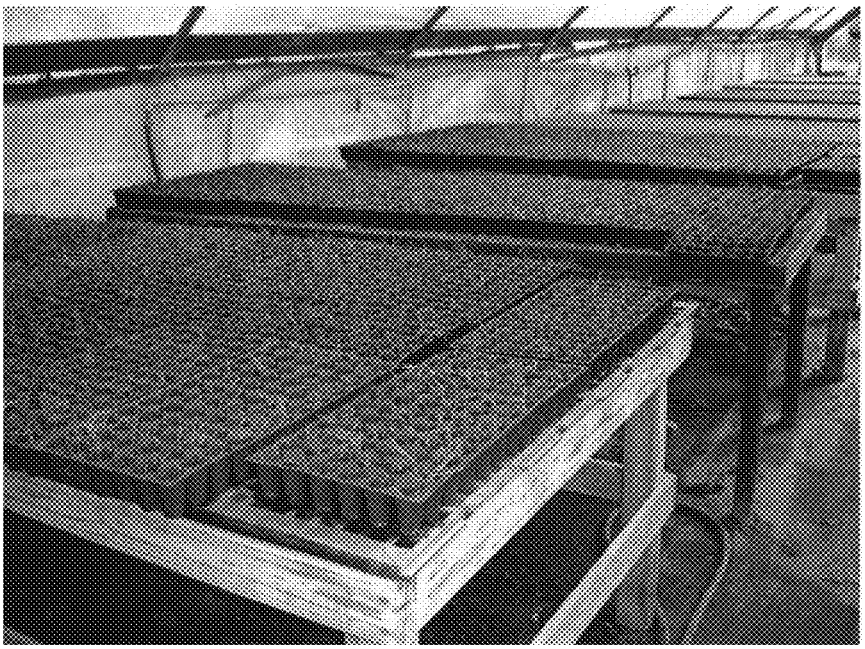
FIG. 5: 'SS-0705' plug tray production.
Figure 6:
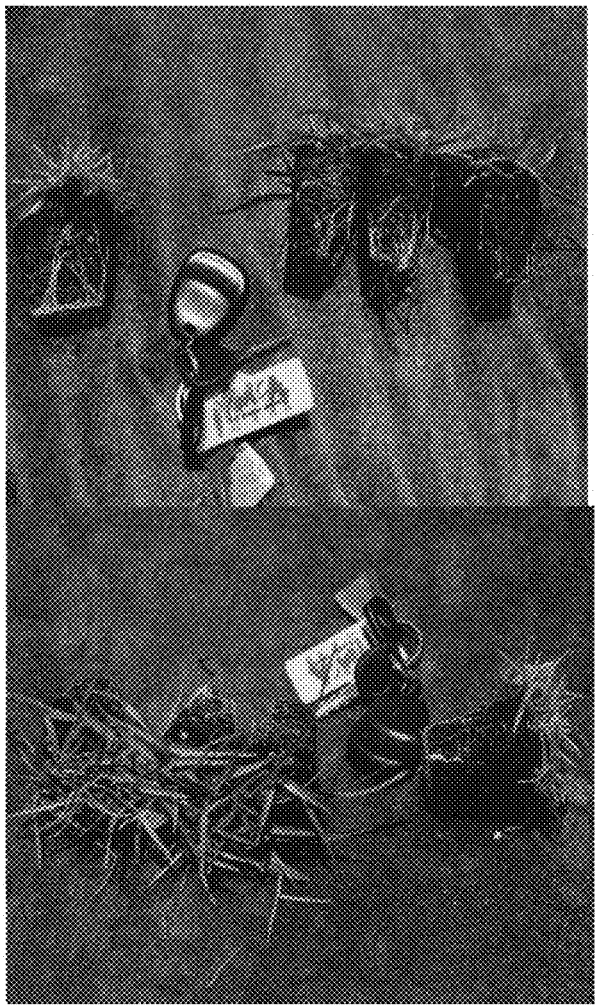
FIG. 6: 'SS-0705' plug detail.
Figure 7:
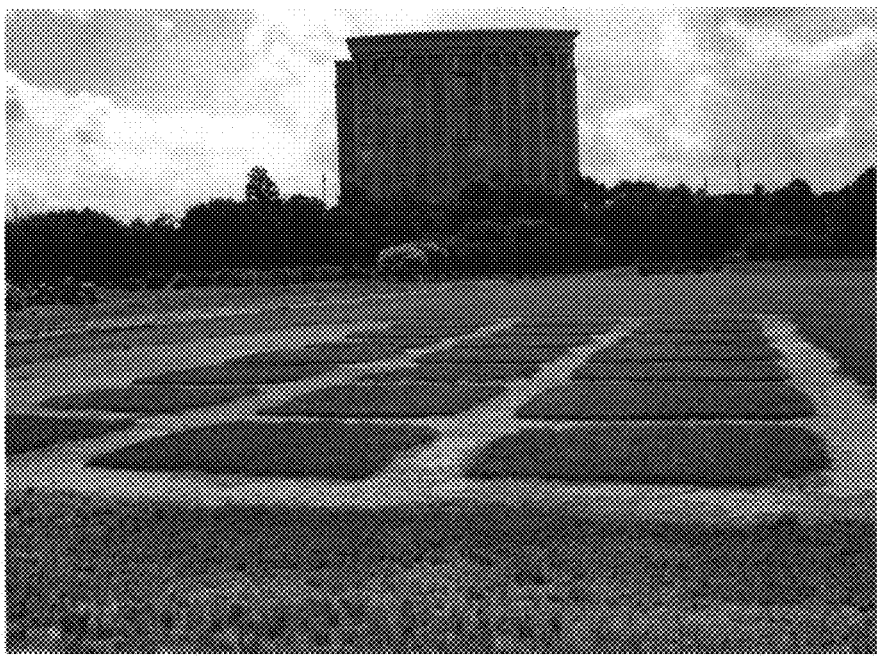
FIG. 7: Test plots with 'SS-0705' near Baton Rouge, La.

A second comparison study was established in a research area near Baton Rouge, La. in March of 2009 (FIG. 7). Test plots were planted on the ground using plugs produced in 128 cell plug tray, using sprigs of the following varieties and experimental lines: 'Common Centipede', 'TifBlair', 'SS-0607' and 'SS-0705'. Trays were filled with Redi-earth Plug and Seedling Mix (Sungro Horticulture, Bellevue, Wash.) and a sprig with 3 internodes was planted on each cell (FIG. 5). Trays were irrigated and kept on a greenhouse until cells developed a matured and rooted plug (FIG. 5). After mature (FIG. 6), plugs of each variety were planted on 5×7 ft. plots with 3 reps and using 12 inches centers. Plots were irrigated, fertilized, mowed and kept free of weeds and insects. After 100% grown in, plots were used to collect morphological data of each variety.

TABLE 4

Analysis of Variance for Centipedegrass cultivars comparisons conducted during the 2009 growing season.

| | Mean Squares of the traits | | | |
|---|---|---|---|---|
| Source | ID (mm) | IL (mm) | LW (mm) | LL (mm) |
| Variety | 2.26** | 502.0** | 0.84 | 1101.4** |
| Error | 0.1 | 22.3 | 0.62 | 250.1 |
| CV | 13.8 | 36.7 | 17.4 | 29.3 |

ID Internode Diameter, IL Internode Length, LL Leaf Width (mm), LW Leaf Length (mm)
Significant at 5% level **Significant at 1% level Cultivars showed significant differences on the following morphological characteristics: Internode Diameter (ID), Internode Length (IL) and Leaf Length (LL). The above mentioned means were significantly different at 1% level (Table 4). The evaluations were well conducted and produced reliable results as demonstrated by the low Coefficients of Variation (CV) (Table 4).

A distinctive characteristic of 'SS-0705' is its short leaf blade and internode length. Table 5 shows 'SS-0705' with the shortest internode length (10.8 mm) among the tested varieties. The internode lengths of 'Common centipede' (14.3 mm), 'TifBlair' (11.9 mm) and 'SS-0607' (14.5 mm) were statistically different than 'SS-0705' at 5% level (Table 5). 'SS-0705' also exhibits the shortest leaf blade length (48.2 mm) compared to 'Common Centipede' (56.3 mm), 'TifBlair' (53.4 mm) and 'SS-0607' (58.1 mm) (Table 5); being statistically different than 'Common Centipede', 'TifBlair' and 'SS-0607' at 5% level (Table 5).

Small internode diameter and short internode length (Tables 2 and 5), allow 'SS-0705' to exhibit a more dense canopy and adequate density. Combined with a strong and deep root system, those characteristics produce a perfect piece of sod, making harvesting more uniform and with less waste.

Furthermore, low aggressiveness and less nitrogen requirements enables 'SS-0705' to be maintained with little mowing and lower inputs, making it ideal for a low maintenance lawn.

TABLE 5

Morphological measurements from mowed field plots - November, 2009.

| Cultivar | Internode diameter (mm) | Internode length (mm) | Leaf blade width (mm) | Leaf blade length (mm) |
|---|---|---|---|---|
| 'SS-0607' | 2.1 | 14.5 | 4.4 | 58.1 |
| 'Common centipede' | 2.0 | 14.3 | 4.7 | 56.3 |
| 'TifBlair' | 2.1 | 11.9 | 4.5 | 53.4 |
| 'SS-0705' | 1.9 | 10.8 | 4.5 | 48.2 |
| LSD(0.05) | 0.1 | 1.0 | NS | 5.7 |
| Number of observations | 150 | 150 | 60 | 60 |

Figure 8:
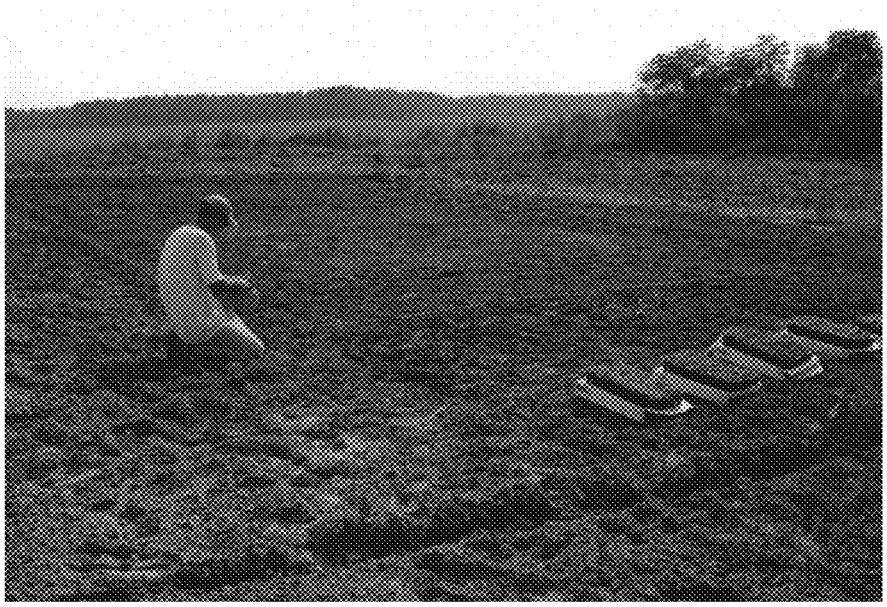
FIG. 8: Test plot area being planted with plug trays during 2009.
Figure 9:
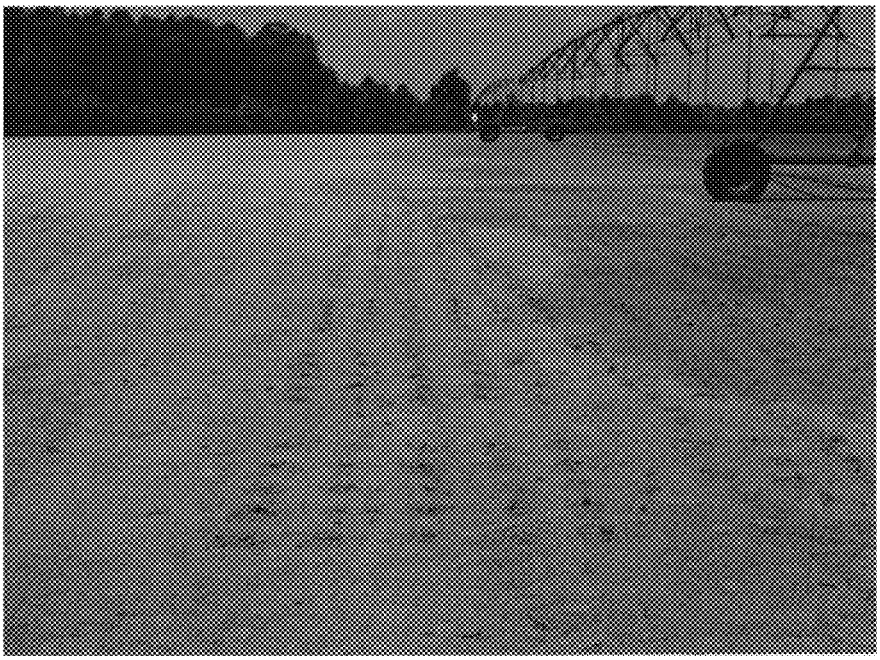
FIG. 9: Test plot are after planted with plug trays, in 2009.

A third set of test plots was planted at sod farms in TX, NC, SC, AL and GA during 2009 (FIGS. 8 and 9); using the same plug trays produced as described previously. Plots had the same dimensions (5×7 ft. with 3 reps) and plugs were planted using the same spacing (12 inch centers).

'SS-0705' proved to have low aggressiveness and it was the cultivar with the third to lowest % of ground cover by August 10 (90.0%) (Table 6), most like due to its short internode length (Tables 2 and 5).

TABLE 6

% of Cover of 'SS-0705' and other cultivars at 5 locations in 2009.

| # | Cultivar | Jun. 21 | Jul. 13 | Jul. 25 | Aug. 10 | Aug. 31 |
|---|---|---|---|---|---|---|
| 1 | 'SS-0705' | 31.7 | 76.7 | 81.7 | 90.0 | 100.0 |
| 2 | 'J1' | 41.7 | 83.3 | 90.0 | 89.0 | 99.7 |
| 3 | 'J2' | 30.0 | 71.7 | 76.7 | 81.7 | 96.7 |
| 4 | 'SS-0607' | 38.3 | 81.7 | 85.0 | 94.0 | 100.0 |
| 5 | '1Z2' | 50.0 | 85.0 | 90.0 | 92.7 | 100.0 |
| 6 | 'TifBlair' | 36.7 | 81.7 | 81.7 | 89.0 | 100.0 |
| 7 | 'Common centipede' | 43.3 | 83.3 | 85.0 | 92.3 | 100.0 |
| | LSD (0.05) | 8.5 | 6.5 | 8.2 | 6.9 | NS |

That which is claimed is:

1. A new and distinct variety of Centipedegrass named 'SS-0705', as herein illustrated and described, characterized by its distinctive and unique combination of several characteristics such as: green stolons, white flowers, short inflorescence, short and narrow leaf blades.

* * * * *